United States Patent [19]

Mos et al.

[11] Patent Number: 4,590,044
[45] Date of Patent: May 20, 1986

[54] MULTISTAGE REACTOR FOR EXOTHERMIC OR ENDOTHERMIC CHEMICAL PROCESSES

[75] Inventors: Arie L. Mos; Franciscus H. J. Bukkems, both of The Hague, Netherlands

[73] Assignee: Shell Oil Company, Houston, Tex.

[21] Appl. No.: 539,897

[22] Filed: Oct. 7, 1983

[30] Foreign Application Priority Data

Oct. 7, 1982 [NL] Netherlands ............... 8203894

[51] Int. Cl.⁴ .............. B01J 10/00; B01J 14/00; F28D 21/00
[52] U.S. Cl. ................... 422/191; 422/194; 422/203; 422/205; 422/207; 422/224
[58] Field of Search .......... 422/193, 194, 203, 205, 422/207, 224, 256, 260, 191; 261/123, 153

[56] References Cited

U.S. PATENT DOCUMENTS

| | | | |
|---|---|---|---|
| 2,390,430 | 12/1945 | Dons et al. | 422/260 X |
| 2,974,020 | 3/1961 | Kassel | 422/219 X |
| 3,433,600 | 3/1969 | Christensen et al. | 422/194 X |
| 3,445,533 | 5/1969 | Mottern | 261/123 X |
| 3,455,658 | 7/1969 | Wilkinson | 422/207 X |
| 3,963,423 | 6/1976 | Dorr et al. | 422/207 X |
| 4,071,322 | 1/1978 | Graat | 422/203 |

FOREIGN PATENT DOCUMENTS

| | | |
|---|---|---|
| 742356 | 11/1969 | Belgium . |
| 499653 | 6/1930 | Fed. Rep. of Germany . |
| 2161523 | 7/1973 | France . |

Primary Examiner—David L. Lacey
Assistant Examiner—Brion P. Heaney
Attorney, Agent, or Firm—Ronald R. Reper

[57] ABSTRACT

A reactor is disclosed for carrying out exothermic or endothermic chemical reactions in which the reaction temperature is maintained as constant as possible. The reactor comprises a reaction space, an inlet for at least two reaction components, and an outlet for the reaction products. The reactor according to the invention is characterized in that the reaction space is provided with a plurality of interconnected reactor stages through which the reaction stream passes in succession, that each reactor stage comprises three reaction component guiding means, and that each reactor stage is provided with at least one injection opening for at least one reaction component.

9 Claims, 1 Drawing Figure

U.S. Patent
May 20, 1986
4,590,044
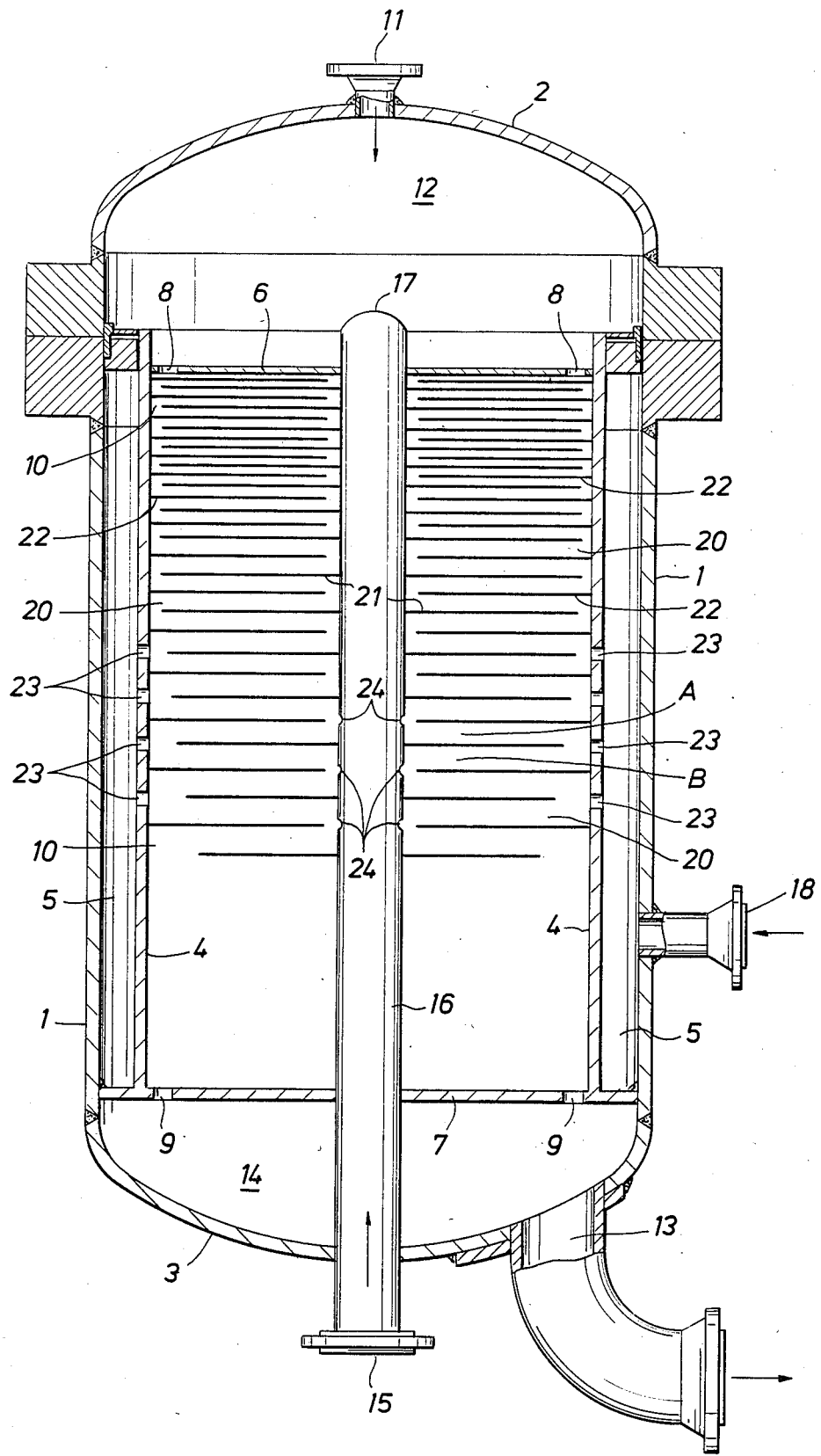

MULTISTAGE REACTOR FOR EXOTHERMIC OR ENDOTHERMIC CHEMICAL PROCESSES

BACKGROUND OF THE INVENTION

The invention relates to an apparatus for carrying out exothermic and endothermic chemical reactions in which the reaction temperature is maintained as constant as possible, said apparatus comprising a reaction space, an inlet for at least two reaction components, and an outlet for the reaction products.

When carrying out exothermic or endothermic chemical processes it is genrally important that the temperature within the reactor is maintained within a relatively narrow range in order that the process should proceed as well as possible. In addition, it is important that the added reaction components should be homogeneously distributed in order to obtain a high yield of the main product and a low production of by-product(s). Moreover, the reactor should be compact and easy to dismantle in order to facilitate maintenance thereon.

It has often turned out to be necessary in existing reactors to install extensive measuring and control equipment in order to achieve satisfactory operation, which involves considerable costs.

The apparatus according to the invention overcomes these drawbacks and provides a relatively simple reactor which meets the above requirements.

SUMMARY OF THE INVENTION

In accordance with the present invention there is provided a multi-stage reactor apparatus suitable for exothermic and endothermic chemical reactions which reactor comprises:

A. a closed reactor shell confining a reaction space,

B. a first inlet means for a first reaction component in direct fluid communication with said reaction space in a first reaction stage, and adapted to be connected to a first reaction component source, C. a plurality of reaction component guiding means within said space defining a plurality of interconnected reaction stages through which the first reaction component stream passes in succession from first to a final reaction stage, D. a second inlet means for a second reaction component, said means being in direct fluid communication with each of the reaction stages, and adapted to be connected to a second reaction component source, E. a third inlet means for a temperature moderating component in direct fluid communication with a substantial number of said interconnected reaction stages, and F. reaction mix outlet means in direct fluid communication with the final reaction stage, whereby during operation of the reactor, the reaction temperature within said reaction space can be maintained relatively constant.

BRIEF DESCRIPTION OF THE DRAWING

FIG. 1 is a cross-section in axial direction representation of a reactor constructed in accordance with the invention.

GENERAL DESCRIPTION OF THE PREFERRED EMBODIMENTS

The invention is characterized in that the reaction space is provided with a plurality of interconnected reactor stages through which the reaction stream passes in succession, that each reactor stage comprises a plurality of reaction component guiding means and that each reactor stage is provided with at least one injection opening for at least one reaction component.

The invention provides a compactly built reactor which is simple to install, maintain and dismantle.

The invention will be further explained with reference to the drawing, showing a cross-section in axial direction of an embodiment of a reactor according to the invention, wherein the reaction component guiding means are radially arranged lamellae.

Although in the drawing the reactor is arranged in such a position that its longitudinal central axis extends in a vertical direction, it is observed that this is not necessary for satisfactory operation. Different positions are possible, for example the reactor can be arranged in such a position that its central axis extends in a horizontal direction.

The reactor according to the drawing comprises a cylindrical outer shell 1 provided at one end with a cover 2 and at the opposite end with a cover 3. Within the outer shell 1 an inner shell 4 is arranged in such a manner that an annular space 5 is formed between the outer shell 1 and the inner shell 4. The inner shell 4 is provided at one end with an end plate 6 and at the opposite end with and end plate 7. The end plate 6 is provided with a large number of openings 8, for example eight, and the end plate 7 is provided with a large number of openings 9, for example twenty. A reaction space 10 is enclosed by the shell 4 and the end plates 6 and 7.

The cover 2 is provided with first inlet means 11 for a relatively hot first reaction component, which can flow from the inlet 11 through a space 12 between cover 2 and end plate 6 and then through the openings 8 into the reaction space 10.

The cover 3 is provided with a reaction mix (product) outlet 13, so that the product obtained in the reaction space 10 can flow from the reaction space 10 through the openings 9 and through a space 14 between cover 3 and end plate 7 towards the product outlet 13.

The cover 3 is furthermore provided with a second inlet means 15 for a second reaction component which communicates with a central inlet tube 16 which is closed at the end 17.

The outer shell 1 is provided with a third inlet means 18 for a temperature moderating component which may advantageously be the first reaction component supplied at a relatively low temperature. The temperature moderating component may be an inert material but preferably is the first reaction component at a lower temperature than the temperature of the first component entering inlet 11 (for exothermic reactions), or said first component at a higher temperature than the temperature of the first component entering inlet 11 (for endothermic reactions). The inlet 18 communicates with the annular space 5.

The reaction space 10 is subdivided in a large number of reactor stage 20. These reactor stages 20 are connected sequentially with one another and comprise a number of radially disposed reaction component guiding means, for example, lamellae 21 and 22. The lamellae 21 contact the central inlet tube 16 but do not contact the inner shell 4 and the lamellae 22 contact the inner shall 4 but do not contact the central inlet tube 16. The lamellae 21 alternate with the lamellae 22 so that a zigzag path is formed in the reaction space 10. The number of stages is in the range from about 10 to about 25.

Most or all reactor stages 20 have at least one direct fluid communication (i.e., injection) opening 23 in the inner shell 4 for injecting the temperature moderating component into the reactor stages 20.

Each injection opening 23 should have a suitable diameter, for example, a diameter in the range of from 1 to 3 mm. For the sake of clarity only a few injection openings 23 are shown schematically. The number of injection openings 23 per reactor stage 20 can vary, for example, from 10 to 25.

Each reactor stage 20 is additionally provided with at least one direct fluid communication (injection) opening 24 for the second reaction component. The injection openings 24 are arranged in the wall of the central inlet tube 16. For the sake of clarity only a few openings 24 are shown schematically. The number of injection openings 24 per reaction stage 20 can vary, for example, from 8 to 12. The injection openings 24 should have a suitable diameter, for example, a diameter in the range of from 1 to 2 mm.

The operation of the reactor according to the invention is as follows:

A first, relatively hot, reaction component is supplied to the inlet 11. This first hot reaction component flows from inlet 11 through space 12 and openings 8 into the reaction space 10. The alternating lamellae 21 and 22 cause the first reaction component to flow through the successive reactor stages 20, according to a zigzag path. A second reaction component is supplied to the inlet 15 and is passed from inlet 15 through central inlet tube 16 and through the injection openings 24 into each reactor stage 20. Since the second reaction component is passed at high speed, preferably at critical speed, through the relatively small injection opening 24 into each reactor stage 20, the second reaction component and the first reaction component are quickly and intensively mixed. The first reaction component is also supplied to inlet 18, but at relatively low temperature. From inlet 18 this relatively cool first reaction component passes through the annular space 5 and through the small injection openings 23 into most or all of the reactor stages 20. Since the relatively cool first reaction component is passed at high speed, preferably at critical speed, through the relatively small injection openings 23 into the corresponding reactor stages 20, the relatively cool first reaction component is mixed quickly and intensively with the hot first reaction component the second reaction component and the reaction product present in the reactor stages 20. The relatively low temperature of this addition is necessary, since otherwise the temperature would not remain within the desired limits for the exothermic reaction between the first and second reaction components.

It will be clear that the temperature at the shell 4 of each reactor stage 20, which has increased by the reaction between the components, will be lowered by the injection of the first reaction component at relatively low temperature.

Each reactor stage 20 may be divided in two sections, viz. a first section A between openings 24 and 23 wherein mainly the reaction between the first and second reaction components takes place and a second section B between openings 23 and 24 wherein no, or substantially no, reaction takes place, but wherein mainly cooling of the mixture occurs. Each reactor stage therefore consists of three lamellae, two attached to the reactor shell and one lamellae attached to the central inlet tube.

After the reaction components have passed through the various reactor stages 20 and have completed the desired reaction, the reaction product mix obtained passes through the openings 9, space 14 and leaves the reactor through product outlet 13.

Injection through the injection openings 23 and 24 is done at high speeds, preferably at critical speeds, so that the large differences in velocities ensure good and quick mixing of the reaction components. The distance between the lamellae increases towards the product outlet 13, for example from 20 to 78 mm, in order to obtain approximately equal residence times of the reaction mixture, e.g., 100 ms, between successive injection openings.

It will be obvious to those skilled in the art that if the reactor is used for carrying out an endothermic reaction the first reaction component supplied through inlet 11 should be at a relatively low temperature, while the injection via openings 23 should be at a relatively high temperature.

The reactor according to the invention can in particular be used advantageously for the allyl chloride process, wherein propene at a temperature of about 450° C. is used as the relatively hot first reaction component (supplied via inlet 11), chlorine as the second reaction component (supplied via inlet 15), and propene at a temperature of about 10°–20° C. as the relatively cool first reaction component (supplied via inlet 18).

In this case the temperature in the reactor according to the invention is maintained at a fairly constant temperature of 480°–520° C. A homogeneous distribution of the two reaction components propene and chlorine is achieved and the production of by-products is small. Moreover, only useful by-products are produced.

In the embodiment of the reactor as described, the reaction component guiding means are radially arranged lamellae. Instead, it is possible to use lamellae extending in an axial direction.

If desired the lamellae 21 and/or 22 can be attached to a suitable holder (not shown) mounted in the reactor.

We claim:

1. A multi-stage reactor apparatus suitable for exothermic and endothermic chemical reactions between at least two reaction components which reactor comprises:
  (A) a closed reactor shell confining a reaction space wherein said reaction space contains a plurality of reaction stages,
  (B) a first inlet means for a first reaction component in direct fluid communication with said reaction space, for directing said first component solely into a first reaction stage and capable of being connected to a first reaction component source,
  (C) a second inlet means for a second reaction component, said second inlet means being an axially aligned conduit within said reaction space and in direct fluid communication with each of the reaction stages and capable of being connected to a second reaction component source,
  (D) a plurality of reaction component guiding means consisting of successive radially disposed lamellae within said space defining a zigzag path through a plurality of interconnected reaction stages through which the first reaction component steam passes in succession from said first to a final reaction stage, wherein each reactor stage consists of the portion of reaction space between three successive lamellae, wherein two lamellae of each reactor stage are attached to the reactor shell, while another lamellae is attached within said reaction space to said second inlet means, said another lamellae being situated between the aforementioned two lamellae, and adjoining the inlet of one of the reaction components, and the number of sequential reaction stages is in the range from about 10 to 25, (E) a third inlet means for a temperature moderating component in direct fluid communication with a substantial number of said interconnected reaction stages, said third inlet means being capable of being connected to a temperature moderating source, and (F) reaction mix outlet means disposed in direct fluid communication with the final reaction stage, whereby during operation of the reactor, the reaction temperature within said reaction space can be maintained relatively constant.

2. Apparatus according to claim 1, wherein the distance between the lamellae increases towards the outlet of the reaction products.

3. Apparatus according to claim 1, wherein the distance between the lamellae varies from 20–78 mm.

4. Apparatus according to claim 1, wherein the second inlet means consists of 8–12 openings per reactor stage.

5. Apparatus according to claim 4, wherein the diameter of each said opening is 1–3 mm.

6. Apparatus according to claim 1 wherein said third inlet means comprises at least one direct fluid communication opening per successive reaction stage provided at the reactor periphery.

7. Apparatus according to claim 6, wherein the third inlet means comprises a plurality of openings within said reactor shell axially positioned between the second inlet means for successive reactor stages.

8. Apparatus according to claim 6, wherein said third inlet means consists of 10–25 openings per reactor stage.

9. Apparatus according to claim 8, wherein the diameter of each said opening is 1–3 mm.

* * * * *